United States Patent
Barbe-Vicuna et al.

[11] Patent Number: 5,800,245
[45] Date of Patent: Sep. 1, 1998

[54] COMPRESSION BRASSIERE AND PAD FOR MANUAL LYMPHATIC DRAINAGE

[75] Inventors: Lucrecia Barbe-Vicuna, Oisterwijk; Han Peter Hamers, Esbeek, both of Netherlands

[73] Assignee: Lucrecia Barbe-Vicuna, Tilburg, Netherlands

[21] Appl. No.: 602,732

[22] PCT Filed: Aug. 18, 1994

[86] PCT No.: PCT/NL94/00195

§ 371 Date: Apr. 18, 1996

§ 102(e) Date: Apr. 18, 1996

[87] PCT Pub. No.: WO95/05095

PCT Pub. Date: Feb. 23, 1995

[30] Foreign Application Priority Data

Aug. 18, 1993 [NL] Netherlands ............... 9301432

[51] Int. Cl.$^6$ ............... A41C 3/00; A41C 3/12
[52] U.S. Cl. ............... 450/57; 450/1; 2/267; 2/73
[58] Field of Search ............... 2/73, 267; 450/1, 450/30, 31, 32, 53, 54, 55, 56, 57; 607/108; 128/874, DIG. 19

[56] References Cited

U.S. PATENT DOCUMENTS

| | | | |
|---|---|---|---|
| 1,190,602 | 7/1916 | Sorkin | 450/1 |
| 1,272,427 | 7/1918 | Haderlein | 450/58 X |
| 1,620,335 | 3/1927 | Farkas | 450/1 |
| 2,333,434 | 11/1943 | Middlecoff | 450/55 |
| 2,641,763 | 6/1953 | Schroeder | |
| 2,886,820 | 5/1959 | Morris | 450/91 |
| 3,196,464 | 7/1965 | McKee | 450/57 X |
| 3,221,748 | 12/1965 | Glasser | 450/56 |
| 3,293,663 | 12/1966 | Cronin | 623/8 |
| 3,430,632 | 3/1969 | James et al. | 450/1 |
| 3,521,642 | 7/1970 | Jordan | 450/70 X |
| 3,641,592 | 2/1972 | Den Bleyker | 623/7 |
| 4,023,575 | 5/1977 | Nixon | |
| 4,071,914 | 2/1978 | Silverman | 450/57 X |
| 4,879,766 | 11/1989 | Hull et al. | 450/1 |
| 4,955,909 | 9/1990 | Ersek et al. | 623/8 X |
| 5,149,293 | 9/1992 | Gable | 450/1 |
| 5,180,326 | 1/1993 | Williams | 450/31 X |
| 5,211,598 | 5/1993 | Hall | 450/1 |
| 5,395,280 | 3/1995 | Greenberg | 450/55 X |
| 5,429,593 | 7/1995 | Matory | 450/1 |
| 5,538,502 | 7/1996 | Johnstone | 450/1 X |

FOREIGN PATENT DOCUMENTS

| | | | |
|---|---|---|---|
| 0151623 | 10/1951 | Australia | 450/56 |
| 958.747 | 3/1950 | France | |
| 88 11 089.3 | 11/1988 | Germany | |
| 89 03 376.0 | 8/1990 | Germany | |
| 91 07 681.1 | 1/1992 | Germany | |

Primary Examiner—Jeanette E. Chapman
Attorney, Agent, or Firm—Young & Thompson

[57] ABSTRACT

Brassiere made of elastic material, the cup assembly of which is constructed, around the two cups, at least with shoulder straps and side panels which merge into a back panel. The shoulder straps and/or the side panels are of broadened design. The brassiere is provided, on the side next to the body, with a complete lining accessible for compression pads, or is provided, on the side next to the body with lining pockets (5) in selected positions, in which compression pads (10) of resilient material can be removably accommodated. At least one lining pocket for accommodating a compression pad (11) can also be provided in the cups of the cup assembly and/or in the back panel. The compression pad is composed of a thin strip of resilient material, such as foam rubber, and has chamfered edges. The strip can be covered with seam-free material, or is accommodated in lining pockets of thin seam-free material, and has, for example, a thickness of at least 1 cm. The strip has a smooth surface, at least on a pressure side, which surface can be provided with small grooves.

12 Claims, 5 Drawing Sheets

COMPRESSION BRASSIERE AND PAD FOR MANUAL LYMPHATIC DRAINAGE

The invention relates to a brassiere, the cup assembly of which is constructed, around the two cups, at least with shoulder straps and with side panels which merge into a back panel. Brassieres of this type are known in practice.

In the past, surgery and radiotherapy were generally employed for the treatment of breast cancer. When a mastectomy had taken place, a brassiere of the abovementioned type could then, if appropriate, be provided with one or two external silicone breast prostheses. Over the past 15 years, however, mastectomy has to an ever increasing extent been supplanted by so-called breast-saving (conserving) treatments (BST). In the case of this BST, the surgeon restricts him- or herself to removing the tumour from the breast and (a large proportion of) the lymph nodes from the ipsilateral armpit. The role played by radiotherapy is greater in the case of this treatment than following a mastectomy. The results of BST with respect to survival and to disease-free survival are at least as good as those achieved by mastectomy. However, both after the said treatment and after a mastectomy, problems can arise which, depending on the severity, impede the woman to a greater or lesser extent in going about her normal activities, both in respect of homework and in respect of her employment. The problems involved here are complications such as asymmetry of the breasts, (lymphatic) oedema of the breast and/or of the chest wall, impairments in scar formation, fibrosis, painful areas on the skin of the breast and armpit, and plexopathies.

The abovementioned complications are of subchronic to chronic nature. The measures to be taken against them, such as physiotherapy and keep-fit exercises, therefore have only a temporary effect.

In the interim, extensive experience has clearly shown that manual lymphatic drainage causes the complaints to disappear in a large number of the abovementioned cases. Manual lymphatic drainage (MLD) is a special form of non-forcing and gentle massage. This MLD promotes the re-absorption of tissue fluid in blood and lymphatic capillaries, stimulates the motor response of the lymphatic vessels, as a result of which the transport capacity increases, and makes the hardened or induced tissue supple again and causes the pain to disappear.

As a consequence of the chronic character of the abovementioned complaints, these recur relatively rapidly (for example within a few days) after the end of treatment in the majority of cases. In medical practice, the question therefore arose as to how the result achieved could be consolidated. It was known to use an elastic arm 'sock', which prevents the accumulation of tissue fluid by increasing the tissue pressure from the outside. However, this 'sock' can be used only for extremities, such as arms or legs.

The aim of the invention is to overcome the abovementioned problems and to provide a solution with which the beneficial effects of MLD at the chest, side and/or back wall and/or shoulder girdle can be consolidated. According to the invention, this is achieved with a brassiere of the type mentioned in the preamble, in that the shoulder straps and/or the side panels are of broadened design, in that the brassiere is provided, at least in one location an the side next to the body, with a lining pocket for accommodating a compression pad and in that such a compression pad is made of resilient material in order to increase tissue pressure to consolidate the result achieved by manual lymphatic drainage. A compression pad of this type can comprise a thin strip of resilient material, such as foam rubber, or resilient fibres enclosed in a cushion pocket.

The shape of said compression pad depends on the site of the complaint and accordingly is determined anatomically by the path of the lymph (i.e., tissue fluid) drainage areas which are still available. That is to say, those areas from which tissue fluid still has to be removed and underneath which there are sometimes irreversible fibrotic tissue changes.

The effect of the MLD treatment in the therapeutic stage, after the operation and radiation treatment, is consolidated by means of said design of the brassiere with associated compression pad. The compression pad or pads accommodated in the brassiere consolidate the therapeutic effect. The compression pad provides a non-forcing external pressure on lymphatic oedema of the breast and/or the chest wall, as a result of which the tissue pressure rises and the effect of the MLD is consolidated and an increase in oedema after the end of the MLD is counteracted. This secondary lymphatic oedema can & arise after the operation or after the operation and the radiation treatment. Said oedema is combatted by the MLD, but can return after the end of the MLD.

The impaired scar formation which is experienced in some cases after mastectomy or lymph node excision gives rise to painful hardening and/or oedema in the region of the scar and the area directly surrounding it. An appreciable alleviation can be achieved by MLD and this can be consolidated by means of the abovementioned brassiere and compression pad with the associated lasting pressure. Where scar formation is impaired, there is, namely, question of cord-like tissue hardening. Another problem is the formation or broad areas of hardening, which usually occur in the lower half of the breast and in the region of the armpit. By accommodating compression pads or appropriate shape in the brassiere according to the invention, these abnormalities and complaints can also be successfully treated.

The brassiere with compression pad according to the invention is also important for plexopathias, which are the most troublesome complications of treatment of breast cancer by surgery and radiotherapy. What is involved here is, namely, a combination of tissue hardening and lymphatic oedema in an area rich in nerve tissue. In this case also, reduction and even disappearance of the pain can be achieved by treatment of the tissue hardening and the lymphatic oedema by MLD. Here again, the compression pad can provide for consolidation of the result achieved.

The aim of the said compression (external pressure) is, as has been stated, to increase the tissue pressure, which leads to better absorption of the tissue fluid in blood and lymphatic capillaries: an improvement in the calibre of veins and lymphatic vessels, as a result of which better removal of blood and lymph is achieved; stimulation of the muscle pump (as a result of the external pressure, blood vessels and lymphatic vessels are squeezed "empty" when the muscles contract) and of the lymphatic vasomotor response by the alternating pressure on the lymphatic vessels from the outside (each collecting lymph vessel is individually able to contract actively as a result of the muscle cells present in the wall of the vessel).

Experience has shown that MLD, as a non-aggressive gentle massage technique, can be used successfully in the treatment of a number of pain syndromes. The beneficial effect is explained by the local reduction in the oedema and the rapid removal of the mediators causing the pain. Apart from the desensitising effect on the peripheral pain receptors in the tissue, an analgesic effect on the central nervous system is also ascribed to MLD in the form of a counter-irritation or peripheral stimulation and analgesia in accordance with the Principle of "gate control theory". The use of the compression brassiere after every MLD treatment consolidates the effects of the MLD, inter alia by the vagotonising effect and the stimulated lymphatic vasomotor response, which can last for some hours after a treatment.

The causes of hyperalgesia of the hemithorax with its extensive areas of skin are diverse, such as painful scars, tumorectomy and axillary clearance in the case of breast-saving operations, and puffy fibroses. Haematoma, seroma and infiltrate can become painful fibrotic areas. Inflammations, poorly healing wounds and the like can lead to painful, undesirable accumulation of plasma proteins.

Hyperalgesias can be treated by MLD with excellent results. Stimulation of the lymphatic vasomotor response of the proximal lymph-drainage regions and the lymphostatic painful areas gives rise to an increase in the lymph transport capacity and additionally to an increase in the resorption of the lymphostasis with its large molecule proteins in the lymphatic capillaries. Furthermore, removal via fissures in the tissue is promoted and local hardening in the form of subcutaneous accumulations of plasma proteins or raised puffy fibroses is rendered more supple or is broken down. All of this leads to a rapid change in the pattern of symptoms. Even the first treatment often results in a feeling of relaxation and well-being. Especially in extremely painful cases, as where there is an aspecific inflammatory reaction to radiation treatment, this feeling on the part of the patient can be maintained and increased by use of compression therapy on the treated areas.

The indications for the use of the compression brassiere are, inter alia:

1. Fibrosis, pain and/or oedema in the lateral upper quadrant of the breast.
2. Fibrosis, pain and/or oedema in the medial upper quadrant of the breast.
3. Fibrosis, pain and/or oedema in the lateral lower quadrant of the breast.
4. Fibrosis, pain and/or oedema in the medial lower quadrant of the breast.
5. Painful fibrosis in the armpit.
6. Painful thickening in the side, inter alia at the point where the drain of the axillary clearance of the armpit was inserted.
7. Circumscribed pain in the region of the shoulder blade.
8. Asymmetry of the breasts as a consequence of tissue loss after the surgical intervention.
9. Hyperalgesia of the hemithorax after the operation and/or radiation treatment as a consequence of plasma proteins present in this area.
10. Protection of the lymph drainage area at the shoulder line.
11. Anchoring of the elastic arm 'sock'.
12. In the immediate post-operative period, to prevent seroma, oedema and fibrosis.
13. Pain symptoms in the area of the inlet and outlet sites for iridium needles.
14. Treatment of pain and/or fibrosis in the tumour bed treated with iridium or electron radiation.
15. Treatment of puffy fibroses in the region of large scars.
16. Pain symptoms in the area surrounding the drain in general.
17. Hyperalgesia of the supra- and infra-clavicular region.
18. Hyperalgesia of the supra- and infra-clavicular region with a painful movement-restricting shoulder.

For all of these disorders, a compression brassiere can be used with success, in addition to the MLD.

The compression pad to be accommodated in a lining pocket of the abovementioned brassiere is made from resilient material, such as foam rubber which has a minimum thickness of 1 cm and is produced with rounded or chamfered edges. The resilient material can also comprise loose resilient (for example polyester) fibres. The material is, for example, covered by a thin seam-free material, or the lining pockets we made of a thin seam-free material. The delicate, careful treatment principle of the MLD is also carried through when finishing said compression pad. Any thick or stiff seam in the area of the surface to be treated is counterproductive and stringent demands are therefore laid down for finishing in order to achieve the desired aim.

The foam rubber from which the compression pad is made is in some cases smooth on at least one surface and in other cases is provided with small grooves in said surface, giving rise to individual small compression cushions. It is also possible to produce individual small cushions of resilient material, which—after fixing to the said surface of the compression pad—are able to exert additional pressure on concave parts in the area to be treated.

The compression pad and the individual small cushion can be made to measure, and adjusted, to match the particular disorder and the progress thereof and accommodated in the brassiere in the said lining pockets.

Said lining pockets can be located both in a cup and/or in the side panel, which increases in width towards the armpit, and/or in the back panel and can also be located in the broadened shoulder strap. In a variant, the compression brassiere can be provided with a broadened stomach band which serves to support the abovementioned compression effect.

It is known per se from FR-A-958747 to fit a supporting trim of porous material in the bottom of the cups of a brassiere, to support and improve the volume of the bust in the first instance and secondly to activate the blood circulation. A supporting trim of this type can also absorb a specific perfumed, hormone-containing cream for slow release thereof onto the skin. In the case of the present compression brassiere, the abovementioned activation of the blood circulation would be a distinct disadvantage and have a counterproductive effect on the consolidation of the result achieved by manual lymphatic drainage.

The invention will be explained in more detail with the aid of a few illustrative embodiments, with reference to the drawings, in which.

Figure 4A:
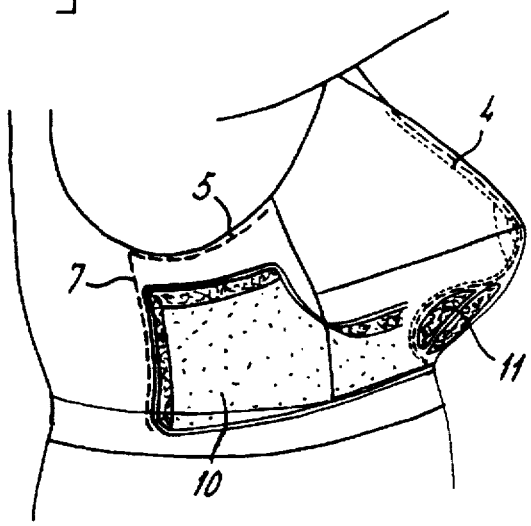
Figure 4B:
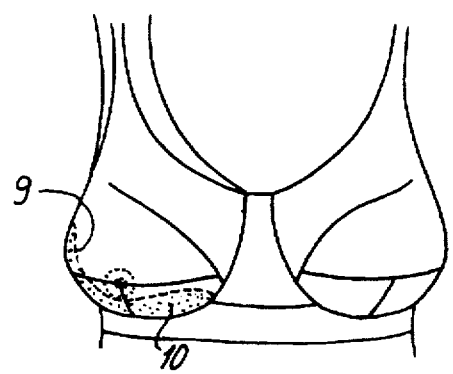
Figure 4C:
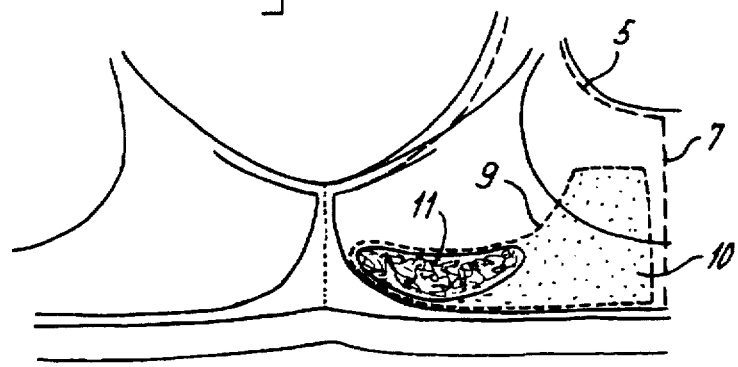
Figure 5A:
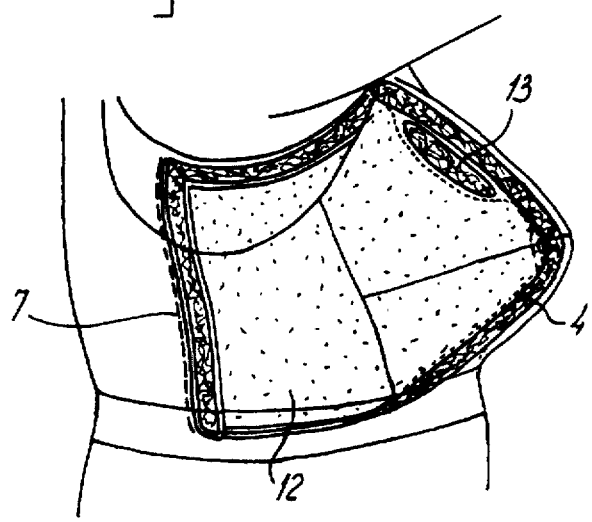
Figure 5B:
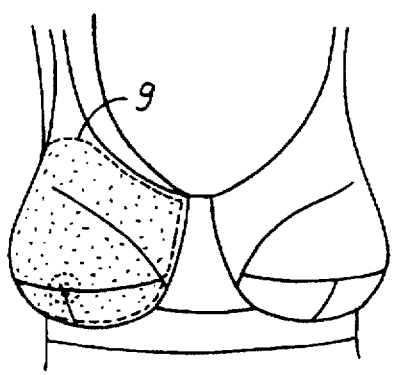
Figure 5C:
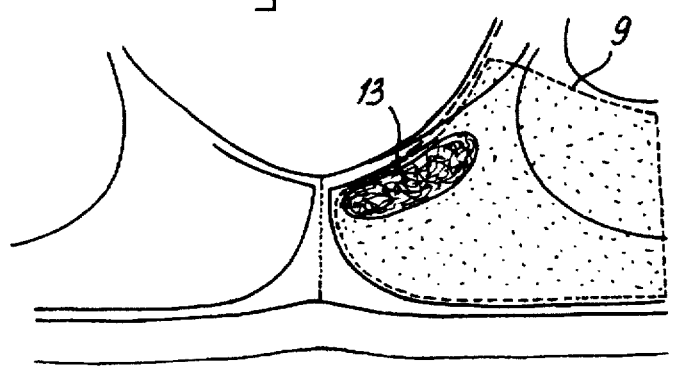

FIGS. 4a to 4c show, respectively, the same views as those shown in FIG. 2, but provided with a compression pad with a supplementary small compression cushion accommodated in a lining pocket; and FIGS. 5a to 5c show, respectively, the same views as those shown in FIG. 2, but provided with a compression pad accommodated in a lining pocket, supplemented by a small compression cushion in another position.

Figure 1A:
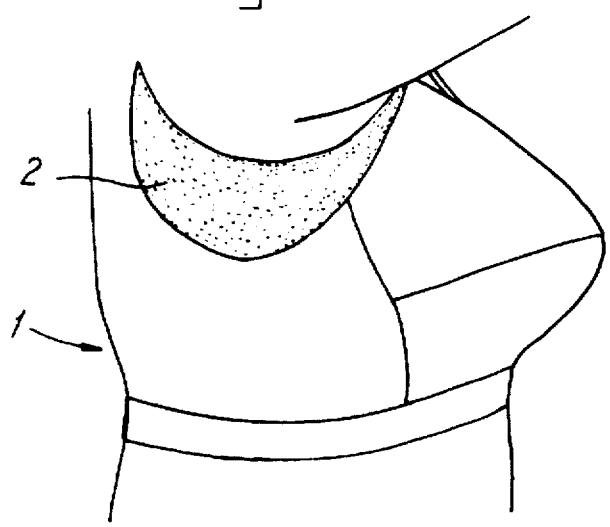
FIGS. 1a to 1c show, respectively, a side view, a front view and a view from the inside of the brassiere according to the invention.
Figure 1B:
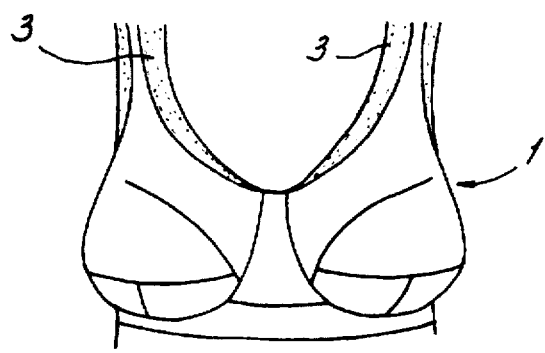
Figure 1C:
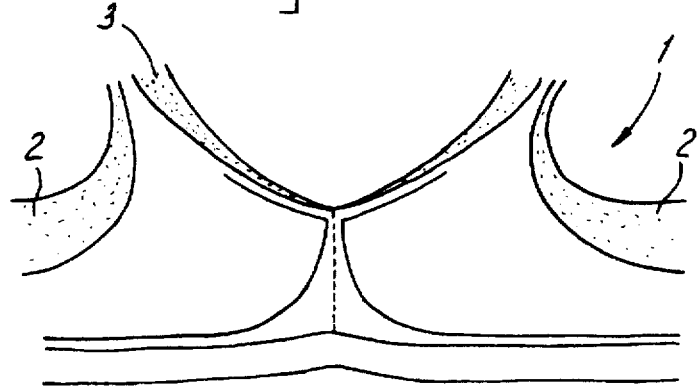

FIGS. 1a and 1b show, respectively, a side view and a front view of a compression brassiere 1 according to the invention, which is made of elastic material and which is provided with possible broadened sections at the cup assembly. Thus, FIG. 1a shows a broadened side panel 2, which can merge into a broadened back panel, and FIG. 1b shows broadened shoulder straps 3. The lower edge of the brassiere could also be broadened by using an additional stomach band. The broadening per se of the side panel and of the shoulder straps is attached, in a manner which is not indicated in more detail, to an existing brassiere or can also be constructed so that it is integral with the latter. FIG. 1c shows a view from, as it were, the body towards the inside of the brassiere. Here, the way in which the broadening of the shoulder strap merges into that of the side panel can be clearly seen. The closure of the brassiere can be either at the front or the back.

Figure 2A:
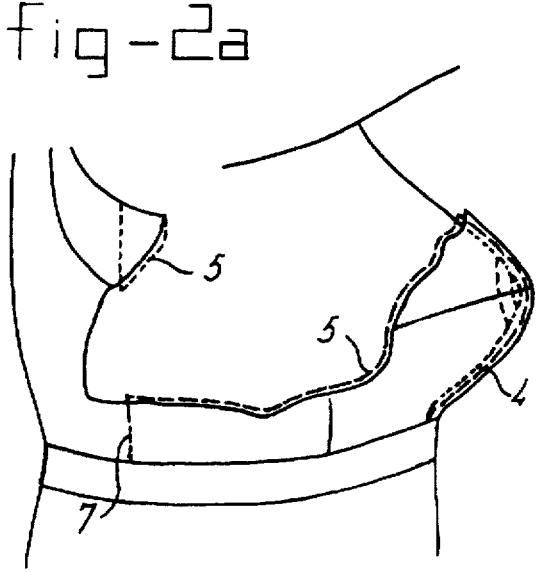
FIGS. 2a to 2c show, respectively, the same views as those in FIG. 1, but with the lining pockets indicated on the drawing.
Figure 2B:
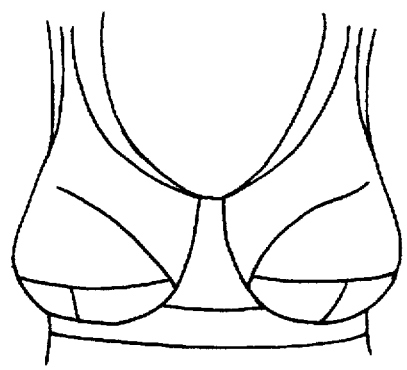
Figure 2C:
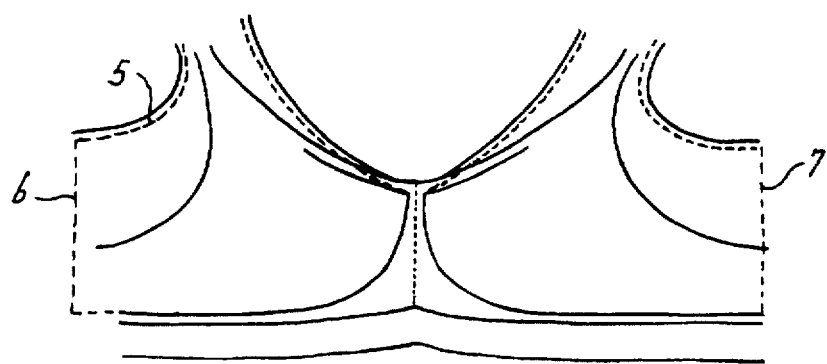

In FIGS. 2a and 2b, the views shown in FIG. 1a and 1b respectively are diagrammatically supplemented by lining pockets, which are indicated by broken lines 5. In FIG. 2a the view is partially exposed and the contour of the skin is indicated by a fine dotted line 4. FIG. 2b is unchanged compared with FIG. 1b. In FIG. 2c the lining pockets are again shown between the broken lines 5. In this example a lining pocket is shown in the right cup and in the left cup. The compression pad and, it appropriate, a small compression cushion can be inserted in the lining pocket in the location indicated by the lines 6 and 7. In the case of a front closure between the two cups, said insertion point can, if necessary, be moved to the back.

Figure 3A:
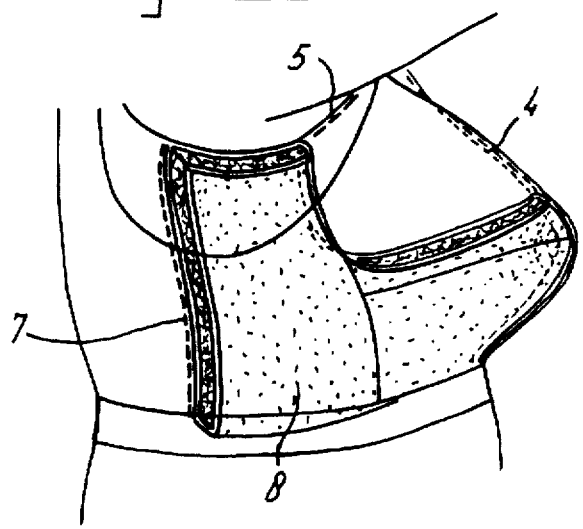
FIGS. 3a to 3c show, respectively, the same views as those shown in FIG. 2, but provided with a compression pad accommodated in a lining pocket.
Figure 3B:
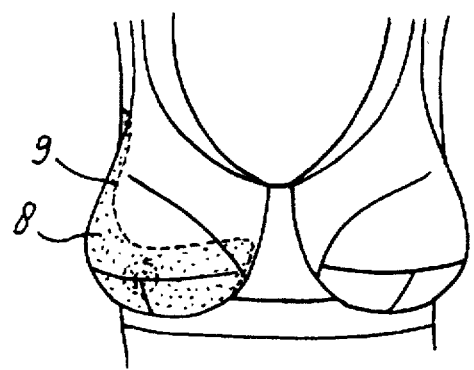
Figure 3C:
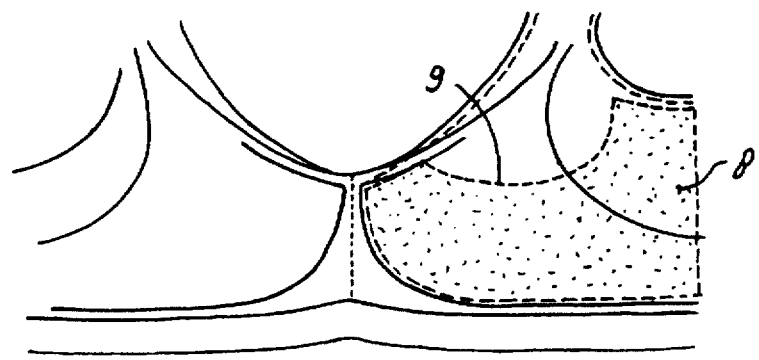

FIGS. 3a to 3c show the way in which a compression pad 8 is accommodated In the lining pocket in the right cup and associated broadened side panel. In this example that portion of the compression pad which is pushed into the lining pocket in the right cup fills three quarters of the cup. The boundary of the compression pad is indicated by the dash-and-dot line 9.

FIGS. 4a to 4c show, for another illustrative embodiment, the way in which another, somewhat narrower, compression pad is accommodated in the right cup and associated side panel, said compression pad in this case being supplemented by the provision of a small compression cushion 11. Said small compression cushion serves for uniform filling-up of the concave area present on the underside of the right breast, in order to support the function of the compression pad.

FIGS. 5a to 5c indicate, for yet a further illustrative embodiment, the way in which yet a further compression pad 12 with associated small compression cushion 13 is accommodated in the right cup and associated broadened side panel. It can again clearly be seen that said small compression cushion 13 serves to fill up the irregular contour at the location of the concave area at the top of the breast, in order to support the function of the compression pad.

It will be clear that a compression pad of this type, optionally in combination with a small compression cushion, can be accommodated in other positions in a lining pocket, for instance in the shoulder strap, in the stomach band or in the back panel. The shape of the compression pad and that of the small compression cushion can be determined depending on the area to be treated. The thickness of the pad and, in particular, that of the small cushion can also be adapted to the treatment.

We claim:

1. A brassiere comprising:

a cup assembly with two cups, shoulder straps, and side panels that merge into a back panel, at least one of said side panels extending upwardly beneath a location of a wearer's axilla and sloping upwardly into the back panel;

a separate lining pocket in said cup assembly in at least one of said side panels extending upwardly beneath the location of the wearer's axilla and sloping upwardly into the back panel, said lining pocket having on a side worn next to a wearer's body a thin seam-free liner; and a compression pad in said lining pocket, said compression pad being made of a resilient material and having a smooth surface on a side worn next to a wearer's body, for increasing tissue pressure and to consolidate an effect of manual lymphatic drainage.

2. The brassiere of claim 1, wherein said compression pad has a shape corresponding to an area of a wearer's body to be compressed.

3. The brassiere of claim 1, wherein said lining pocket is in one of said cups.

4. The brassiere of claim 1, wherein said lining pocket is in one of said shoulder straps.

5. The brassiere of claim 1, wherein said lining pocket is in one of said side panels.

6. The brassiere of claim 1, wherein said lining pocket is in said back panel.

7. The brassiere of claim 1, wherein each of said cups, shoulder straps, side panels and back panel comprise a said lining pocket.

8. The brassiere of claim 1, further comprising a wide stomach band extending downwardly from said cups, side panels and back panel to support a compression effect.

9. The brassiere of claim 1, wherein said compression pad comprises one of foam rubber and a cushion of resilient fibers.

10. The brassiere of claim 1, wherein said compression pad has a uniform thickness of at least one centimeter.

11. The brassiere of claim 1, wherein said compression pad comprises edges that are one of chamfered and rounded.

12. The brassiere of claim 1, wherein said compression pad extends over a location of an area beneath and into a wearer's axilla.

* * * * *